United States Patent [19]

Krbechek

[11] Patent Number: 5,488,161
[45] Date of Patent: * Jan. 30, 1996

[54] OXIMATION PROCESS

[75] Inventor: Leroy O. Krbechek, Santa Rosa, Calif.

[73] Assignee: Henkel Corporation, Plymouth Meeting, Pa.

[*] Notice: The portion of the term of this patent subsequent to Sep. 20, 2011, has been disclaimed.

[21] Appl. No.: 220,130

[22] Filed: Mar. 30, 1994

Related U.S. Application Data

[63] Continuation-in-part of Ser. No. 854,522, Mar. 20, 1992, Pat. No. 5,300,689, and a continuation-in-part of Ser. No. 87,828, Jul. 7, 1993, Pat. No. 5,349,088.

[51] Int. Cl.$^6$ .................................................. C07C 249/08
[52] U.S. Cl. ........................................................ 564/259
[58] Field of Search ............................................. 564/259

[56] References Cited

U.S. PATENT DOCUMENTS

| | | | |
|---|---|---|---|
| 3,449,066 | 6/1969 | Swanson | 23/22 |
| 3,592,775 | 7/1971 | Swanson | 252/182 |
| 4,128,580 | 12/1978 | Matsumoto et al. | 260/566 |
| 4,133,834 | 1/1979 | Pickens | 260/566 |
| 4,507,268 | 3/1985 | Kordosky et al. | 423/24 |
| 4,868,334 | 9/1989 | Mathew et al. | 564/264 |
| 5,300,689 | 4/1994 | Krbechek et al. | 564/259 |

OTHER PUBLICATIONS

Mathur et al., "Laboratory Experiments on Phase–Transfer–Catalyzed Reactions of Neutral Molecules", *J. Chem. Ed.*, 67, p. 273, Mar. 1990.

U.S. patent application Ser. No. 07/854,522, filed Mar. 20, 192.

U.S. patent application Ser. No. 08/087,828, filed Jul. 7, 1993.

J. Chem. Ed., vol. 67, No. 3, issued Mar. 1990, Mathur et al. "Laboratory Experiments on Phase Transfer–Catalyzed Reactions of Neutral Molecules", p. 273.

*Primary Examiner*—Peter O'Sullivan
*Attorney, Agent, or Firm*—Wayne C. Jaeschke; Norvell E. Wisdom, Jr.; Patrick J. Span

[57] ABSTRACT

An improved process for oximation of carbonyl compounds, such as ketones and aldehydes by oximation with hydroxylamine including oximation processes carried out in the presence of a catalytic amount of a phase transfer catalyst comprised of a mixture of an alkyl phenol, such as nonylphenol or dodecylphenol and an organic carboxylic acid, such as 2-ethylhexanoic acid, in the presence of an alkali metal or alkaline earth metal compound. The resulting oximes are useful as metal extractants.

21 Claims, No Drawings

OXIMATION PROCESS

This application is a continuation-in-part application of commonly assigned, U.S. application Ser. No. 07/854,522 filed Mar. 20, 1992 (Attorney Docket No. M 5141 MIN) now U.S. Pat. No. 5,300,689 for an Oximation Process, the entire disclosure of which is hereby incorporated by reference, and of commonly assigned, copending U.S. application Ser. No. 08/087,828 filed Jul. 7, 1993 (Attorney Docket No. M 5293 MIN) now U.S. Pat. No. 5,349,088 for an Oximation Process, the entire disclosure of which is hereby incorporated by reference.

BACKGROUND OF THE INVENTION

1. Field of the Invention

This invention relates to the preparation of oximes from essentially water insoluble carbonyl compounds, i.e. ketones or aldehydes, and in particular to improved processes which employ a phase transfer catalyst. Hydroxyoximes prepared by the improved method are useful as metal extractants.

2. Description of Related Art

As described in U.S. Pat. 4,868,334, oximes are generally produced by reacting an organic carbonyl compound such as an aldehyde or ketone with hydroxylamine, usually generated from a hydroxylamine salt such as hydroxylammonium sulfate or hydroxylammonium chloride.

Current oximation procedures, particularly of long alkyl chain ketones, employ standard oximation processes with an alcohol, such as methanol, as a solvent, hydroxylammonium sulfate and sodium acetate. Since sodium acetate must be anhydrous and is considerably more expensive than sodium carbonate, attempts have been made to employ sodium carbonate in the ketoximation procedure, but other than the two commonly assigned applications noted above, such attempts have not been successful.

U.S. Pat. No. 4,133,834 describes the general preparation of alpha and beta-hydroxyoximes generally useful as extractants for metals such as copper from aqueous solutions and discusses, as exemplary processes, those of U.S. Pat. Nos. 3,449,066 and 3,592,775 relative to the preparation of aliphatic, alpha-hydroxyoximes, from the corresponding acyloins and beta-hydroxyoximes from the corresponding aromatic phenones. In each of the processes the reaction is carried out under reflux conditions with an hydroxylamine salt in an alcohol medium (such as methanol) in the presence of a weak base, such as sodium acetate. Such methods typically required long reaction times for completion, particularly when the oximes included aromatic groups. The U.S. Pat. No. 4,133,834 patent describes a process for reducing the time of reaction by employing catalytic amounts of iron, $Fe^{+2}$ and $Fe^{+3}$. Nawal K. Mathur and Chander K. Narang, in "Laboratory Experiments on Phase-Transfer-Catalyzed Reactions of Neutral Molecules", *J. Chem Ed.*, 67, p. 273, March 1990, describe the oximation of benzophenone by first preparing an aqueous solution of hydroxylammonium chloride (1 equiv/equiv of ketone) in water and neutralizing with sodium hydroxide (1 equiv). This results in high concentration of free hydroxylamine being present all at once, which in large scale operations would present an unsafe condition. To this is added an equal volume of toluene containing 1 equivalent of benzophenone and 1 equivalent (stoichiometric amount) of 2-ethylhexanoic acid at 60° C. for 1.5 hour. In the reaction mixture the level of water is 53.5 moles/mole of carbonyl and the level of toluene was 4.76 g/g of ketone. The 2-ethylhexanoic acid allegedly acts as a bifunctional catalyst, i.e. a weak acid catalyst as well as a phase transfer catalyst.

The oximes, such as the hydroxy aryl ketoximes and hydroxy aryl aldoximes, which are substantially insoluble in water but soluble in water immiscible, organic solvents, such as kerosene, are useful in solvent extraction processes for recovery of metals, particularly copper, from aqueous solutions. U.S. Pat. 4,507,268, describes a number of such oxime reagents prepared from ketones and aldehydes, and the use thereof in liquid/liquid extraction processes.

DESCRIPTION OF THE INVENTION

In this description, except in the operating examples or where explicitly otherwise indicated, all numbers describing amounts of ingredients or reaction conditions are to be understood as modified by the word "about" in describing the broadest scope of the invention. Practice of the invention within the exact numerical limits is however generally preferred.

In Ser. No. 08/087,828, noted above, it was discovered that alkyl phenols having from about 6 to about 20, preferably about 8 to about 18 carbon atoms, when employed in the oximation process catalyze the oximation of carbonyl containing compounds, acting as a phase transfer catalyst.

In application Ser. No. 07/854,522, noted above, it was discovered that carboxylic acids having from about 4 to about 20, preferably about 6 to about 18, carbon atoms also act as a phase transfer catalyst in the oximation of ketone or aldehyde carbonyl compounds. In each of these applications the phase transfer catalyst, carboxylic acid or phenol, acts to accelerate the rate at which the carbonyl compounds, ketones or aldehydes, are oximated. The use of these phase transfer catalysts also provide additional advantages. Firstly, alcohol solvents may be avoided thereby reducing any flammability hazards, as well as eliminating environmental concerns which normally require recovery by stripping of the methanol together with the attendant cost of stripping equipment. Secondly, sodium carbonate may be employed in the process of oximation of the ketones, eliminating the necessity for anhydrous sodium acetate, which is not only expensive, but which also results in the generation of acetic acid in the reaction requiring further treatment and equipment for handling of the acetic acid. Thus, the environmental benefits of the present invention are many.

It has now been discovered that further improvement in the acceleration of the rate at which the ketone or aldehyde carbonyl compounds are oximated, is obtained by the use of a mixture of the carboxylic acids of Ser. No. 07/854,522 and the alkyl phenols of Ser. No. 08/087,828.

One aspect of the present invention accordingly provides for an improved process of oximation of carbonyl compounds (ketones or aldehydes), comprising (a) reacting a carbonyl compound with hydroxylamine in the presence of
  (1) a catalytic amount of a phase transfer catalyst comprising a mixture of an organic carboxylic acid and an alkyl phenol and
  (2) an alkali metal or alkaline earth metal hydroxide or carbonate (including bicarbonate) to form the oxime of said carbonyl compound; and (b) recovering the resulting oxime from the reaction mixture.

The present invention is directed to the oximation of carbonyl compounds, and in particular to oximation of ketones or aldehydes, the oximes of which are useful in the extraction of metal values, such as copper, from aqueous leach solutions. While the process of the present invention may be applied to the preparation of oximes of ketones or aldehydes generally, it is of particular value to the preparation of aromatic oximes useful for extraction of metal values from aqueous solutions, which oximes are substantially insoluble in water but are soluble in water immiscible organic solvents such as kerosene, such as those described in U.S. Pat. 4,507,268 noted earlier above.

The present invention is useful in the preparation of hydroxy aryl ketoximes and aldoximes from the corresponding ketones or aldehydes. Such hydroxy aryl ketoximes and aldoximes are ideally defined by the formulas I and II:

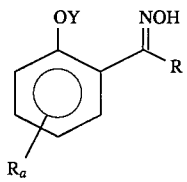
(I)

in which R and $R_a$ may be individually alike or different and are saturated aliphatic hydrocarbon groups of 1–25 carbon atoms or an ethylenically unsaturated aliphatic group of 3–25 carbon atoms and Y is H or $R_b$, and $R_b$ is an aliphatic hydrocarbon group containing 1–10 carbon atoms;

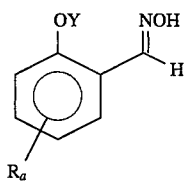
(II)

in which $R_a$ and Y are as defined above with respect to formula I. Preferred compounds of formulas I and II are those in which $R_a$ is a straight or branched chain alkyl group having from 7–12 carbon atoms, and wherein it is attached para to the hydroxyl group. Among these, the more preferred are those wherein $R_a$ is a mixture of isomers. Compounds of formula II which are especially useful in the practice of metal extraction include 2-hydroxy-5-heptylbenzaldoxime, 2-hydroxy-5-octylbenzaldoxime, 2-hydroxy-5-nonylbenzaldoxime and 2-hydroxy-5-dodecylbenzaldoxime. Compounds of Formula I which are especially useful in the practice of metal extraction include 2-hydroxy-5-octylacetophenone oxime and 2-hydroxy-5-nonylacetophenone oxime.

As indicated, the oxime is prepared by oximation of the corresponding ketone or aldehyde with hydroxylamine. The hydroxylamine is preferably employed in the form of a salt thereof, preferably the sulfate, halide (chloride or bromide) or phosphate and the like. The least expensive and most preferred is the sulfate.

The hydroxylamine, preferably the sulfate (hydroxylammonium sulfate), is employed in an amount of at least 1 equivalent to 1 equivalent of carbonyl, and preferably in a slight excess up to about 15 to about 50 equivalent percent, i.e. up to 1.5 equivalents of hydroxylamine to carbonyl. Preferably, the hydroxylamine is employed in an excess amount of about 1.1 equivalent/equivalent carbonyl. Thus, the hydroxylamine will preferably be employed in an equivalents ratio of hydroxylamine to carbonyl greater than 1:1 up to about 1.15 or about 1.2:1 and preferably about 1.1:1.

The reaction of the ketone or aldehyde with hydroxylamine is carried out in the present invention in the presence of a catalytic amount of a phase transfer catalyst comprised of a mixture of an organic carboxylic acid and a phenol. The preferred phenols employed in the mixture are those phenols having branched or straight chain alkyl groups containing from about 6 to about 20 carbon atoms, most preferably about 8 to about 18 carbon atoms. The most preferred phenols employed in the present invention are those containing from 8 to 12 carbon atoms. The alkyl group may be a single straight chain alkyl group or may be a mixture of branched chain isomeric alkyl groups.

The preferred acids employed as a phase transfer catalyst are the weak organic carboxylic acids, aliphatic or aromatic, containing from about 4 to about 20 carbon atoms, most preferably about 6 to about 10 carbon atoms. The preferred acid employed in the present invention is 2-ethylhexanoic acid. Other acids which may be employed are the organo phosphorous or sulfonic acids.

In the phase transfer mixture catalyst the carboxylic acid is preferably employed in amounts up to about 0.2 moles of acid per mole of carbonyl compound, preferably from about 0.001 to about 0.1 moles acid/mole of carbonyl, with about 0.04 moles acid/mole of carbonyl being most preferred.

The phenol in the phase transfer catalyst mixture is preferably employed in catalytic amounts up to about 0.5 moles of phenol per mole of carbonyl, preferably from about 0.05 to about 0.3 moles phenol/mole of carbonyl, with about 0.15 to about 0.2 moles phenol/mole of carbonyl being most preferred.

The reaction of the hydroxylamine with the carbonyl compound (ketone or aldehyde) is conducted in the presence of an alkali metal or alkaline earth metal hydroxide or carbonate (including bicarbonate). While sodium carbonate is preferred, the other alkali metal carbonates may be employed such as potassium or lithium carbonate. Calcium carbonate is preferred as an alkaline earth metal carbonate replacement for the sodium carbonate.

The alkaline compound is employed in at least a stoichiometric amount to the hydroxylamine salt, i.e. at least 1 equivalent carbonate to 1 equivalent hydroxylamine salt, although a slight excess is preferred up to about 15 to about 50% excess. Thus, the carbonate will preferably be employed in an equivalent ratio of carbonate to hydroxylamine greater than 1:1, up to about 1.5:1, most preferably about 1.1:1.

While not intended to be limited thereto, the reaction is believed to proceed as indicated below. The phenol and acid mixture serves as a phase transfer catalyst and reacts at the surface of the sodium carbonate to form the corresponding sodium salts and water. The sodium salts can then react at the surface of the hydroxylammonium sulfate to form sodium sulfate and the hydroxylammonium salts. The resultant hydroxylammonium salts are soluble in the organic phase and can react with the ketone or aldehyde to form the desired oxime, water and regenerate the catalyst. The presence of the phase transfer catalyst permits the use of lower temperatures, while retaining reasonable time periods.

Water should be present, preferably only in an amount sufficient to wet the surfaces of the hydroxylammonium sulfate and sodium carbonate crystals. As Raschig hydroxylamine contains water, no added water is required. If none of the reactants or solvent media contain any water, where the system would otherwise be an anhydrous one, a small amount of water, sufficient to wet the surfaces of the hydroxylammonium sulfate and sodium carbonate crystals, will preferably be added. Accordingly, water is preferably present in the reaction mixture, either added water or by product water of reaction and may be present up to an amount of about 10 moles of water per mole of carbonyl, preferably at least about 0.1 mole water/mole of carbonyl. Preferably the water will be present in an amount of about 0.5 mole to 5 moles water/mole of carbonyl with about 1 mole water/equivalent carbonyl being most preferred.

The reaction may be conducted in the absence of solvent. It is, however, preferred to carry out the reaction employing a hydrocarbon solvent, such as toluene. The presence of the hydrocarbon solvent provides several advantages. The toluene solvent serves to thin the reaction mixture somewhat to prevent excessive foaming. The hydrocarbon solvent also promotes better dispersal of the reaction components thereby providing further reduction in reaction time. The presence of the solvent, such as toluene, also provides a safety feature as the temperature may be kept fairly constant at the toluene-water azeotrope reflux temperature, thereby minimizing any hazard which may be associated with the use of hydroxylamine at high temperatures. Toluene is the preferred hydrocarbon solvent, however other inert, aliphatic or aromatic solvents may be employed, such as xylene, hexane, heptane, ethers and kerosene.

The reaction in the present invention will be complete, or substantially complete in from about 1 to 7 hours, dependent on the particular temperature of reaction. With aldehydes, such as 5-nonylsalicylaldehyde or 5-dodecylsalicylaldehyde, the operative temperature range may extend from ambient temperatures of about 25° C. up to about 95° C., with about 50 to about 90° C. being preferred. With ketones, such as 2-hydroxy-5-nonylacetophenone, the temperature will extend from about 50° to about 95° with temperatures above about 60° C. being preferred, temperatures of about 75° C. to about 90° C. being the most desirable, most preferably about 90° C. With the presence of a hydrocarbon solvent such as toluene, the reaction will be generally conducted at the reflux temperature.

The reaction is preferably conducted with agitation (stirring) to reduce the reaction time. At preferred temperatures of 75°–90° C., with agitation, the reaction will generally be complete within about 4 to about 6 hours. After completion of the reaction, the oxime reaction product is generally diluted further with toluene, followed by a water wash. The first water wash will be very high in salts, which may tend to precipitate on cooling. Accordingly, until diluted, this wash water should preferably be kept hot, i.e. 40°–50° C.

In the foregoing description, the oximation has been described employing both a phase transfer catalyst and an alkaline compound (hydroxide, carbonate or bicarbonate). The alkaline compound is employed preferably in a buffering capacity in a hydrocarbon solvent such as those earlier described, although the reaction may be conducted in the absence of hydrocarbon solvent. Again water is present in amounts as earlier described above. This aspect of the invention is particularly applicable to the preparation of 5-alkylsalicylaldoximes from the corresponding aldehydes in which the alkyl groups have from about 6 to about 12 carbon atoms, preferably about 8 to about 12 carbon atoms.

Accordingly, this invention is particularly adapted to a process for the preparation of alkylaryloximes in which the alkyl group contains from about 6 to about 12 carbon atoms comprising:

(i) reacting an alkylsalicylaldehyde or a 2-hydroxy-5-alkylacetophenone in which the alkyl groups contain from about 6 to about 12 carbon atoms with hydroxylamine in the presence of a catalytic amount of a phase transfer catalyst comprised of a mixture of an alkylphenol and an organic carboxylic acid, and (x) an alkaline compound selected from the group of an alkali metal or alkaline earth metal hydroxide, carbonate and bicarbonate, and (y) water in an amount sufficient to wet the surfaces of the hydroxylamine and the alkaline compound; and (ii) recovering the resulting oxime from the reaction mixture.

The earlier description in relation to oximation of aldehydes as to the reactants, amounts and conditions of reaction apply. The preferred salicylaldehydes and 2-hydroxy-5-alkylacetophenones are the heptyl, octyl, dodecyl and most preferably the nonylsalicylaldehyde and 2-hydroxy-5-nonylacetophenone. The preferred hydroxylamine source is hydroxylamine sulfate and the preferred alkaline compounds are sodium hydroxide or sodium carbonate. Where a hydrocarbon solvent is employed, toluene is preferred. The preferred temperature of reaction is from about 60 to about 90° C. The preferred amounts of the materials are the same as earlier described.

To further illustrate the various objects and advantages of the present invention, the following examples are provided in which all parts and percentages are by weight unless otherwise indicated. It is understood that the examples are entirely illustrative and in no way intended to limit the scope of the invention.

EXAMPLE 1

In this example, the preparation of 2-hydroxy-5-nonylacetophenone oxime (HNAO) from 2-hydroxy-5-nonylacetophenone (HNA) is illustrated, in which nonylphenol is employed alone as the phase transfer catalyst, part A, and the experiment then repeated, part B, adding a carboxylic acid (2-ethylhexanoic acid) to illustrate the use of a mixture of acid and phenol as the phase transfer catalyst. The results can be seen in Tables A and B.

Procedure

The starting material contained 94.3% 2-hydroxy-5-nonylacetophenone HNA) and less than 0.1% nonylphenol.

A mixture of 55.57 g of HNA (0.2 moles), 32.0 g of toluene, 6.6 g of nonylphenol[NP] (0.03 moles), 13.4 g of sodium carbonate (0.126 moles) and 18.13 g (0.11 moles) of hydroxylamine sulfate [HAS] were combined and heated to 75° while stirring with a paddle stirrer at 350 RPM. The HNA had a concentration of 2.0 moles/1. When the temperature had stabilized 3.62 g of water (0.2 moles) was added. The stirred mixture was held at 75°. Samples were withdrawn periodically, diluted with toluene, washed twice with water, the volatiles removed and the residue analyzed by high pressure liquid chromatography (HPLC) for HNA and 2-hydroxy-5-nonylacetophenone oxime (HNAO).

TABLE A

| | (phenol alone) | | |
|---|---|---|---|
| | | | % Residual HNA converted/HR |
| T 1 hr | 10.4% HNAO | 73.1% HNA | 12.8 |
| T 2 hr | 30.3% HNAO | 55.4% HNA | 23.4 |
| T 4 hr | 55.7% HNAO | 30.6% HNA | 22.0 |
| T 8 hr | 71.6% HNAO | 13.4% HNA | 13.9 |

TABLE B (repeat experiment with addition of acid)

|       |             |           | % Residual HNA converted/HR |
|-------|-------------|-----------|------------------------------|
| T 1 hr | 28.3% HNAO | 57.7% HNA | 30.5 |
| T 2 hr | 54.1% HNAO | 32.3% HNA | 43.2 |
| T 4 hr | 72.3% HNAO | 13.2% HNA | 29.4 |
| T 8 hr | 78.9% HNAO | 3.8% HNA  | 17.8 |

EXAMPLE 2

In this example the procedure of example 1 was followed carrying out the oximation with no added phenol phase transfer catalyst and with 0.77 grams (0.005 moles) of 2-ethylhexanoic acid (2-EHA) alone as the phase transfer catalyst.

Procedure

A mixture of 55.57 g of HNA (0.2 moles), 38.05 g of toluene, 13.4 g of sodium carbonate (0.126 moles) and 18.13 g of HAS (0.11 moles) were combined and heated to 75° while stirring with a paddle stirrer at 350 rpm. Again, the HNA had a concentration of 2.0 moles/l. When the temperature had stabilized 3.62 g of water (0.2 moles) was added. Samples were isolated and analyzed as in Example 1.

The results can be seen in Tables C and D below.

TABLE C (no added PTC)

|        |             |           | % Residual HNA converted/HR |
|--------|-------------|-----------|------------------------------|
| T 1 hr | 3.3% HNAO*  | 90.9% HNA | 3.4  |
| T 2 hr | 8.1% HNAO   | 84.9% HNA | 6.4  |
| T 4 hr | 33.3% HNAO  | 61.3% HNA | 13.4 |
| T 8 hr | 65.6% HNAO  | 29.8% HNA | 12.6 |

*Calculated, the found value of 0.90 was below the level at which the instrument was calibrated and considered to be quite inaccurate.

TABLE D (with 2-EMA)

|        |             |           | % Residual HNA converted/HR |
|--------|-------------|-----------|------------------------------|
| T 1 hr | 25.3% HNAO  | 69.8% HNA | 24.9 |
| T 2 hr | 52.6% HNAO  | 44.5% HNA | 35.3 |
| T 4 hr | 74.4% HNAO  | 20.0% HNA | 27.3 |
| T 8 hr | 86.4% HNAO  | 6.7% HNA  | 16.6 |

The foregoing illustrates the effects of a mixture of phenol and carboxylic acid as a phase transfer catalyst in the process of oximation of a carbonyl compound, in contrast to the use of a phenol or an acid alone. As can be seen, the effect is at least an additive one, if not synergistic, at the levels of catalyst and reactants employed.

While nonylphenol was employed with the nonylacetophenone so that the alkyl group of the carbonyl compound being oximated was the same as the alkyl group of the phenol, as in the case of the commonly assigned, copending application Ser. No. 08/087,828, noted earlier, it is not necessary that the alkyl groups correspond and the phenol present in the mixture of phenol and acid phase transfer catalyst may contain other alkyl groups such as heptyl, octyl or dodecyl in catalyzing oximation of a nonyl carbonyl compound. Further, when the carbonyl compound to be oximated is prepared from a phenol, the residual phenol present from the carbonyl compound preparation may be retained in the carbonyl compound itself and from the phase transfer catalyst mixture by the addition of only the carboxylic acid for the mixed phase transfer catalyst. If the alkyl group of the phenol is different from that of the carbonyl compound to be oximated, it is of course added to the reaction mixture prior to the reaction.

While the invention has been exemplified herein employing 2-hydroxy-5-nonylacetophenone as the carbonyl compound being oximated, it is to be understood that the carbonyl compound may be one of those described in the commonly assigned, copending applications, noted earlier, including aldehyde carbonyl compounds, such as heptylsalicylaldehyde, octylsalicylaldehyde, nonylsalicylaldehyde and dodecylsalicylaldehyde, and ketone carbonyl compounds such as 2-hydroxy-5-octylacetophenone, 2-hydroxy-5-heptylacetophenone and 2-hydroxy-5-dodecylacetophenone.

We claim:

1. In a method of preparing aromatic oximes by reaction of a aromatic ketone or aldehyde carbonyl compound with hydroxylamine the improvement which comprises conducting the reaction in the presence of a catalytic amount of a phase transfer catalyst compound comprising a mixture of an alkyl phenol and an organic carboxylic acid, and an alkali metal or alkaline earth metal hydroxide, carbonate or bicarbonate, the catalyst mixture being present in an amount effective to act as a phase transfer catalyst.

2. A method as defined in claim 1 wherein the carbonyl compound is selected from the group consisting of heptylsalicylaldehyde, octylsalicylaldehyde nonylsalicylaldehyde, dodecylsalicylaldehyde, 2-hydroxy-5-nonylacetophenone, 2-hydroxy-5-heptylacetophenone, 2-hydroxy-5-octylacetophenone and 2-hydroxy-5-dodecylacetophenone.

3. A method as defined in claim 1, wherein said phenol in the phase transfer catalyst is an alkyl phenol in which the alkyl group has from about 6 to about 20 carbon atoms and said acid in the phase transfer catalyst is an organic carboxylic acid containing from about 4 to about 20 carbon atoms.

4. A method as defined in claim 3, wherein the alkyl phenol contains from about 8 to about 18 carbon atoms in the alkyl groups.

5. A method as defined in claim 3, wherein the alkyl phenol in the phase transfer catalyst is present in an amount of about 0.05 to about 0.3 moles of phenol per mole of carbonyl compound.

6. A method as defined in claim 3 wherein the acid present in the phase transfer catalyst mixture contains about 6 to about 10 carbon atoms.

7. A method as defined in claim 6 wherein the acid in the phase transfer catalyst is present in an amount of up to about 0.2 moles of acid per mole of carbonyl compound and the alkyl phenol is present in an amount of about 0.15 to about 0.2 moles of phenol per mole of carbonyl compound.

8. A method as defined in claim 7 wherein the acid is present in an amount of from about 0.001 to about 0.1 moles acid per mole of carbonyl compound.

9. A method as defined in claim 7 wherein the acid is 2-ethylhexanoic acid.

10. A method as defined in claim 1, wherein said carbonate is sodium carbonate.

11. A method as defined in claim 10, wherein said carbonate is present in at least a stoichiometric amount to the hydroxylamine.

12. A method as defined in claim 11, wherein said carbonate is present in an amount of 1.1 equivalents of carbonate to 1 equivalent hydroxylamine.

13. A method as defined in claim 1, wherein said carbonyl compound is 2-hydroxy-5-nonylacetophenone, said alkyl phenol in the phase transfer catalyst is nonylphenol, and the acid in the phase transfer catalyst is 2-ethylhexanoic acid.

14. A method as defined in claim 1, wherein the water content is from about 0.1 to about 10 moles of water per mole of carbonyl compound.

15. A method as defined in claim 14, wherein said reaction is conducted in a non-alcoholic media containing water in an amount just sufficient to wet the surfaces of the hydroxylamine and carbonate reactants.

16. A method as defined in claim 14, wherein the media further comprises a hydrocarbon solvent.

17. A method as defined in claim 14, wherein said hydrocarbon solvent is toluene.

18. A method of preparing a hydroxy oxime having the formula

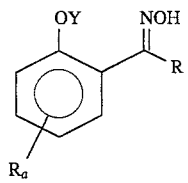 (I)

in which R and $R_a$ may be individually alike or different and are saturated aliphatic hydrocarbon groups of 1–25 carbon atoms or ethylenically unsaturated aliphatic groups of 3–25 carbon atoms and Y is H or $R_b$, where $R_b$ is an aliphatic hydrocarbon group containing from 1 to about 10 carbon atoms; or

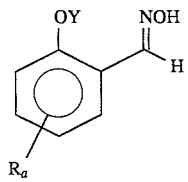 (II)

in which $R_a$ and Y are as defined with respect to Formula I, comprising (a) reacting a carbonyl compound corresponding to the hydroxy oxime defined above with hydroxylamine in the presence of
   (1) a catalytic amount of a phase transfer catalyst comprising a mixture of an alkyl phenol and an organic carboxylic acid; and
   (2) an alkali metal or alkaline earth metal hydroxide, carbonate or bicarbonate;

whereby the carbonyl group of the carbonyl compound is converted to the oxime group; and (b) recovering the resulting oxime from the reaction mixture.

19. A method as defined in claim 18, wherein the alkyl phenol in the phase transfer catalyst contains from about 6 to about 20 carbon atoms in the alkyl group and is present in an amount of about 0.05 to about 0.5 moles of phenol per mole of carbonyl compound, the carboxylic acid in the phase transfer catalyst contains about 6 to about 10 carbon atoms and is present in an amount up to about 0.2 moles of acid per mole of carbonyl compound, the hydroxylamine reactant is hydroxylammonium sulfate present in an amount of about 1.1 equivalents per equivalent of carbonyl, said carbonate is sodium carbonate present in an amount of about 1.1 equivalents carbonate to 1 equivalent of hydroxylamine, and the reaction is conducted at about 50° to about 90° C. in the presence of water in a sufficient amount to wet the surfaces of the hydroxylammonium sulfate and the carbonate.

20. A method as defined in claim 19, wherein the alkyl phenol in the phase transfer catalyst is an alkyl phenol having from about 8 to about 12 carbon atoms in the alkyl group and is present in an amount of about 0.15 to about 0.2 moles of phenol per mole of carbonyl compound, and in which the alkyl group of the alkylphenol is the same as, or different from $R_a$, the carboxylic acid in the phase transfer catalyst is present in an amount from about 0,001 to about 0.1 moles per mole of carbonyl compound and the reaction is conducted with agitation at a temperature of about 90° C. in a non-alcoholic, hydrocarbon solvent reaction media for at least about 1 hour.

21. A method as defined in claim 20, wherein said hydrocarbon solvent is toluene.

* * * * *